(12) United States Patent
Takei

(10) Patent No.: US 9,775,635 B2
(45) Date of Patent: Oct. 3, 2017

(54) HANDLE FOR MEDICAL TREATMENT DEVICE AND MEDICAL TREATMENT DEVICE

(71) Applicant: OLYMPUS CORPORATION, Tokyo (JP)

(72) Inventor: Yusuke Takei, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/077,632

(22) Filed: Mar. 22, 2016

(65) Prior Publication Data

US 2016/0199084 A1 Jul. 14, 2016

Related U.S. Application Data

(63) Continuation of application No. PCT/JP2014/084361, filed on Dec. 25, 2014.

(60) Provisional application No. 61/921,222, filed on Dec. 27, 2013.

(51) Int. Cl.
*A61B 17/29* (2006.01)
*A61B 18/08* (2006.01)
(Continued)

(52) U.S. Cl.
CPC .... *A61B 17/2909* (2013.01); *A61B 17/07207* (2013.01); *A61B 17/295* (2013.01);
(Continued)

(58) Field of Classification Search
CPC ........ A61B 2017/2925; A61B 17/2833; A61B 2018/0091; A61B 2017/2808; A61B 17/285; A61B 17/2909
See application file for complete search history.

(56) References Cited

U.S. PATENT DOCUMENTS 5,632,432 A 5/1997 Schulze et al.
7,156,846 B2 1/2007 Dycus et al.
(Continued)

FOREIGN PATENT DOCUMENTS

JP H08-336540 A 12/1996
JP 2005-193043 A 7/2005
(Continued)

OTHER PUBLICATIONS

Feb. 24, 2015 Search Report issued in International Patent Application No. PCT/JP2014/084361.
(Continued)

*Primary Examiner* — Thomas McEvoy
(74) *Attorney, Agent, or Firm* — Oliff PLC

(57) ABSTRACT

A handle includes a first operation input body provided on a handle main body and configured to rotate in first and second directions to operate a first end effector; an interlock body rotatable relative to the first operation input body; an engaging portion provided in the interlock body and configured to be engaged with the handle main body and to restrict rotation of the first operation input body in the second direction when the first operation input body is rotated in the first direction; and a second operation input body configured to rotate to operate a second end effector, and disengage the engaging portion from the handle main body by pressing the interlock body.

18 Claims, 20 Drawing Sheets

(51) Int. Cl.
*A61B 17/295* (2006.01)
*A61B 17/072* (2006.01)
*A61B 17/32* (2006.01)
*A61B 18/00* (2006.01)

(52) U.S. Cl.
CPC .... *A61B 18/085* (2013.01); *A61B 17/320092* (2013.01); *A61B 2017/07228* (2013.01); *A61B 2017/07264* (2013.01); *A61B 2017/07278* (2013.01); *A61B 2017/2912* (2013.01); *A61B 2017/2925* (2013.01); *A61B 2017/2927* (2013.01); *A61B 2017/2938* (2013.01); *A61B 2018/00589* (2013.01); *A61B 2018/00601* (2013.01); *A61B 2018/00916* (2013.01)

(56) References Cited

U.S. PATENT DOCUMENTS

| | | | |
|---|---|---|---|
| 2005/0107785 A1 | 5/2005 | Dycus et al. | |
| 2005/0139636 A1 | 6/2005 | Schwemberger et al. | |
| 2011/0174862 A1 | 7/2011 | Shelton, IV et al. | |
| 2012/0241503 A1* | 9/2012 | Baxter, III | A61B 17/0643 227/176.1 |
| 2013/0053831 A1 | 2/2013 | Johnson et al. | |
| 2013/0267951 A1* | 10/2013 | Twomey | A61B 18/1445 606/46 |
| 2014/0236152 A1 | 8/2014 | Walberg et al. | |

FOREIGN PATENT DOCUMENTS

| | | |
|---|---|---|
| JP | 2006-095316 A | 4/2006 |
| WO | 2012/118838 A1 | 9/2012 |
| WO | 2013/026884 A2 | 2/2013 |
| WO | 2014/148280 A1 | 9/2014 |

OTHER PUBLICATIONS

Aug. 18, 2015 Office Action issued in Japanese Patent Application No. 2015-529365.
Jul. 7, 2016 International Preliminary Report on Patentability issued in PCT/JP2014/084361.

* cited by examiner

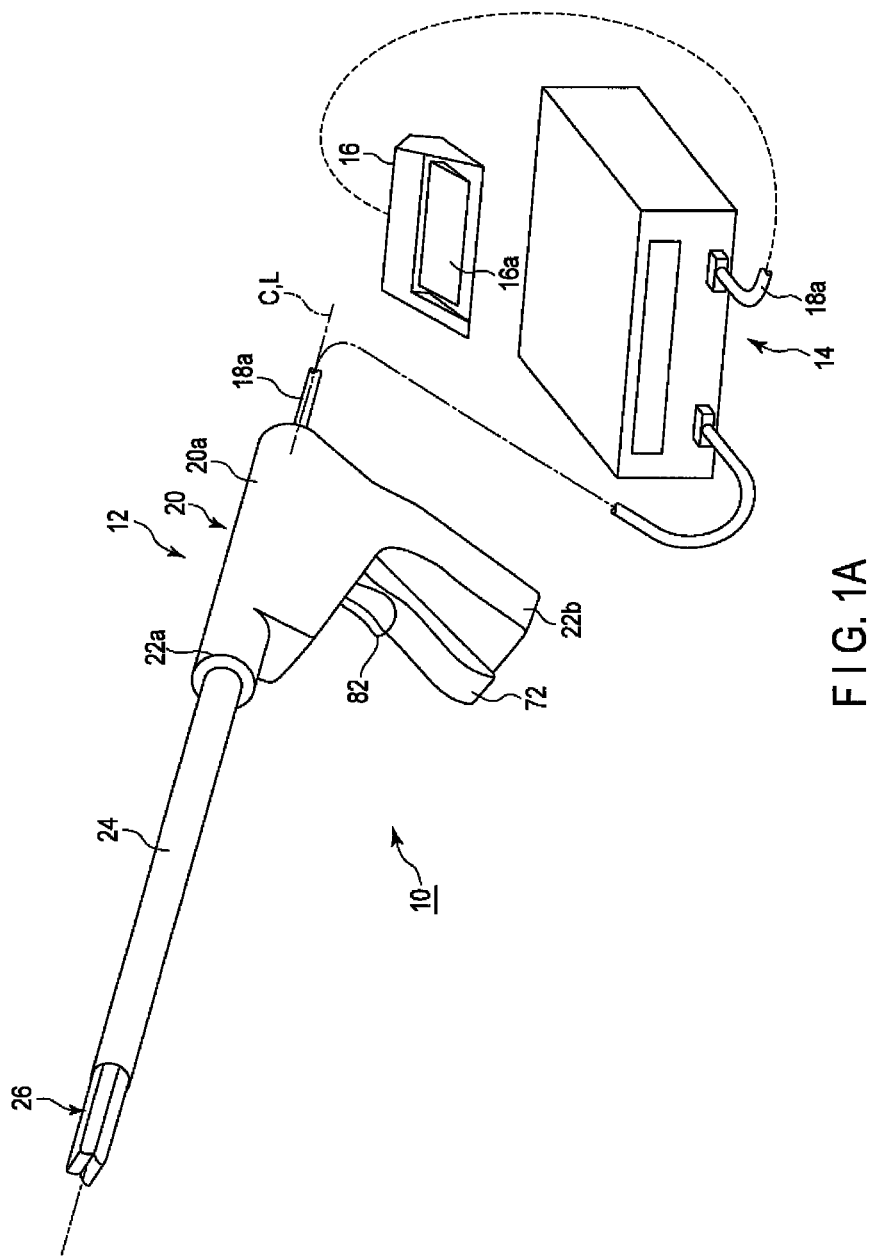
F I G. 1A

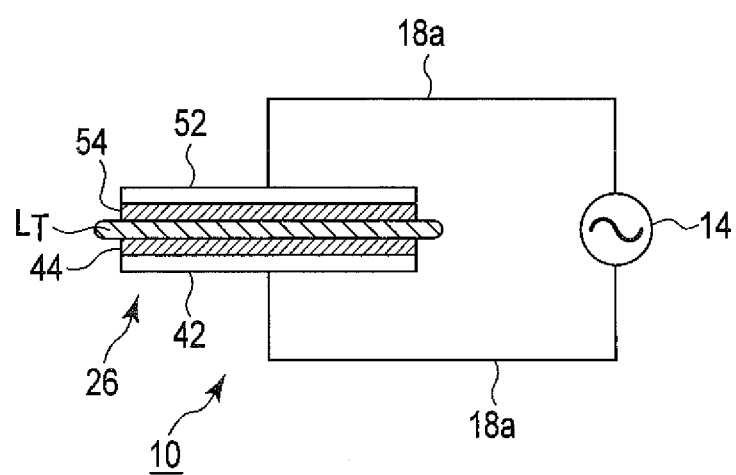
F I G. 1B

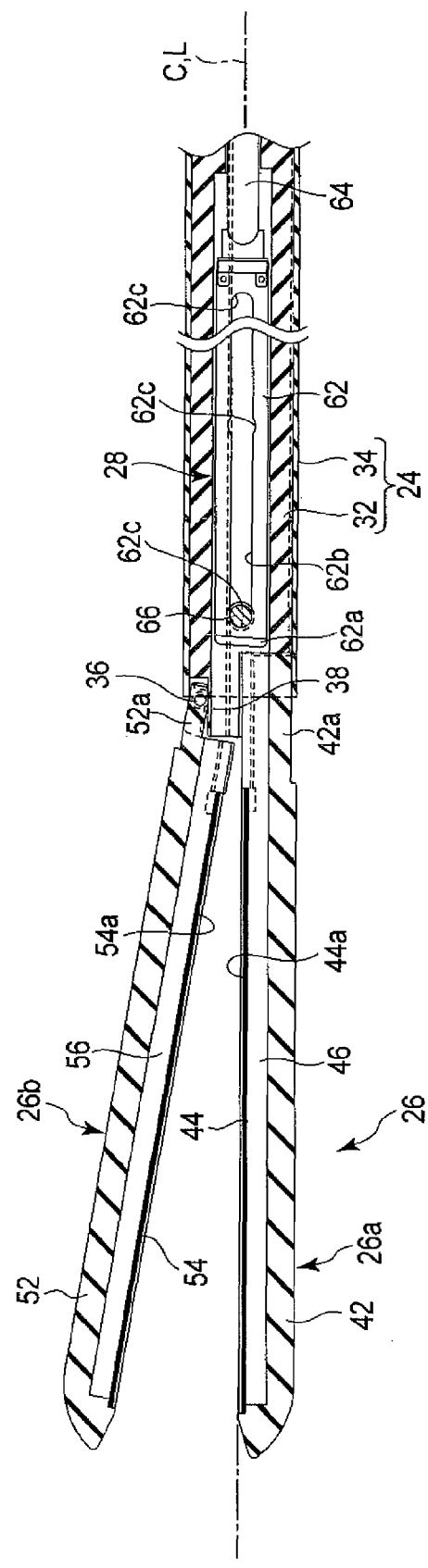
F I G. 2A

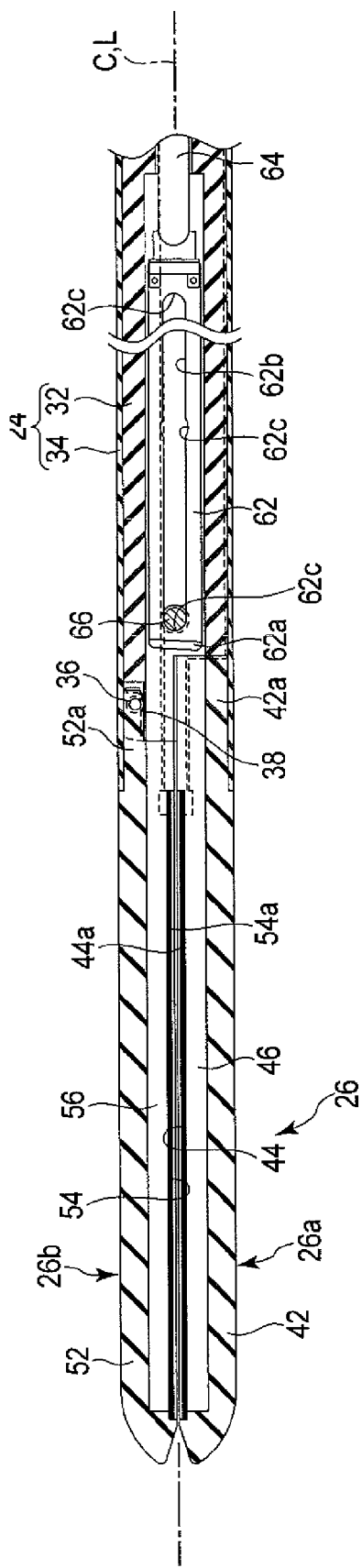
F I G. 2B

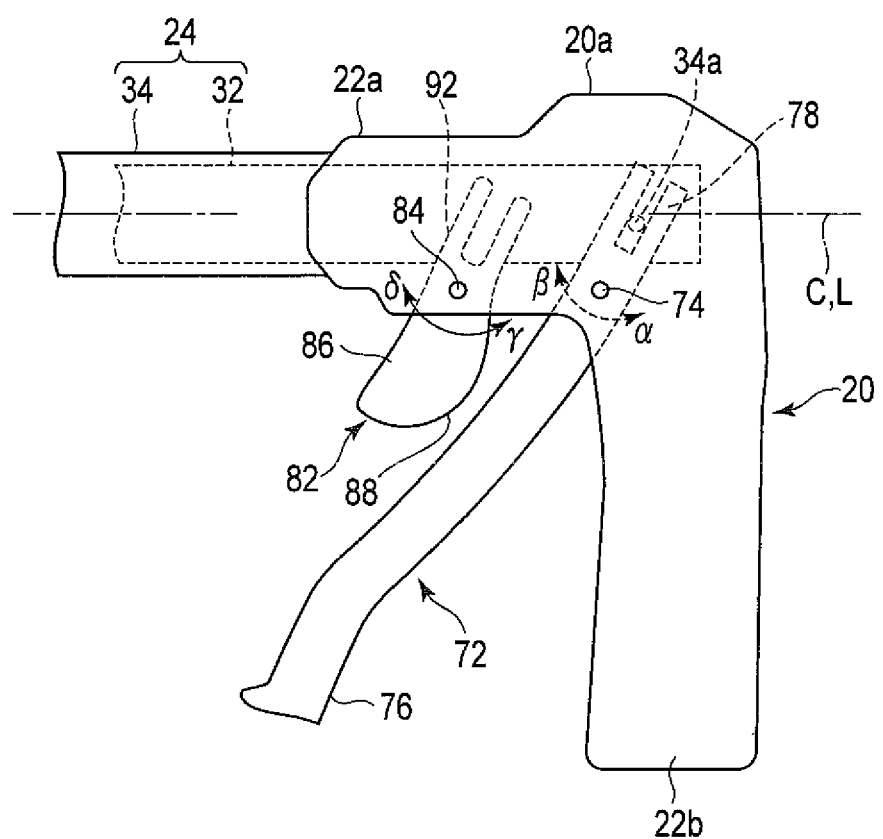
F I G. 3A

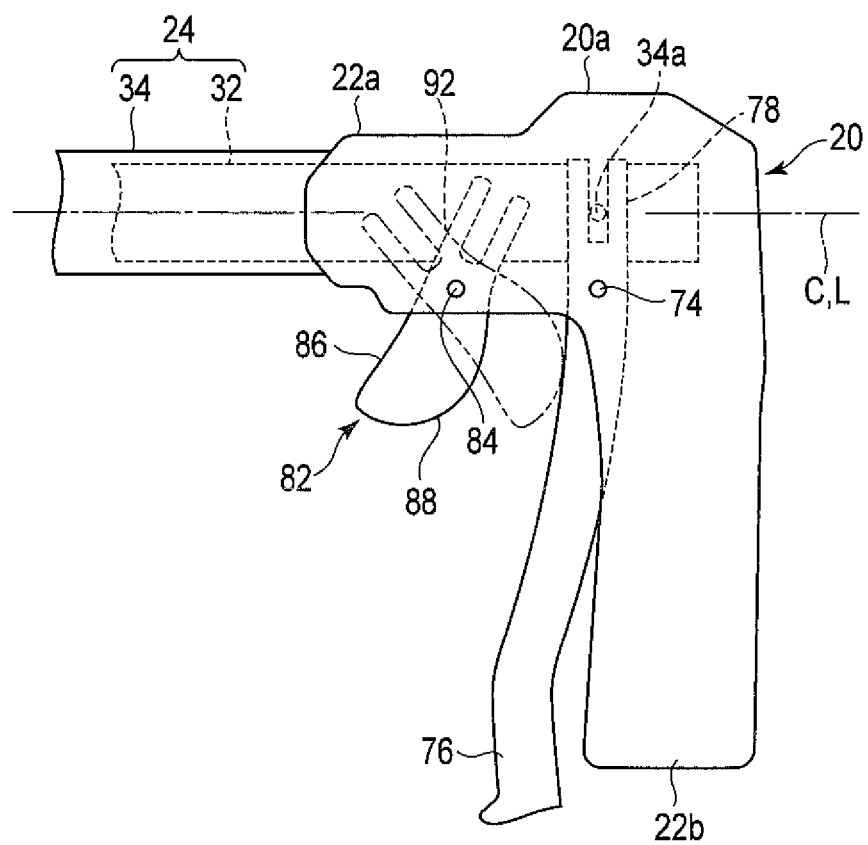
F I G. 3B

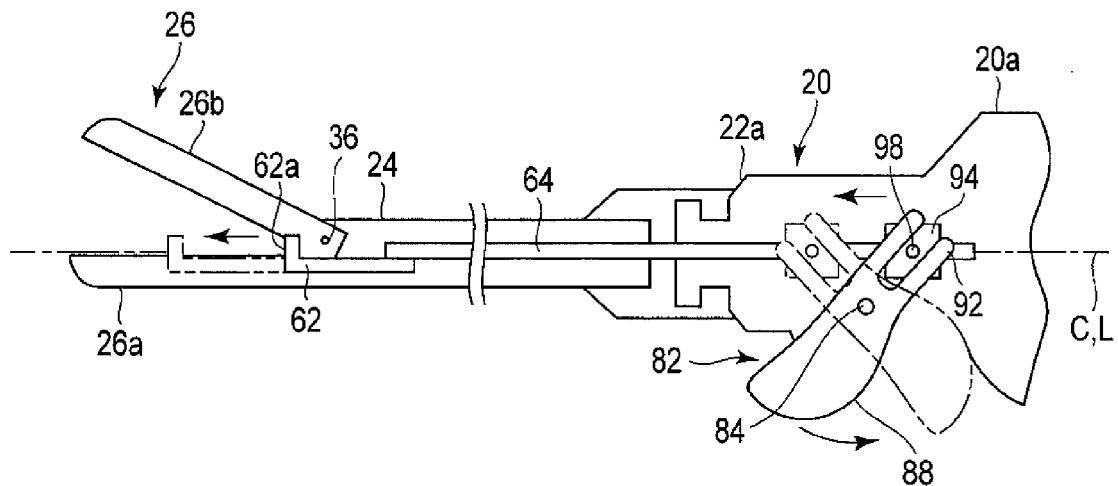
F I G. 4A
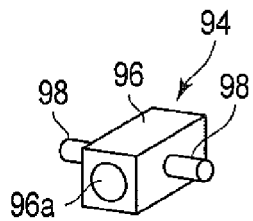
F I G. 4B
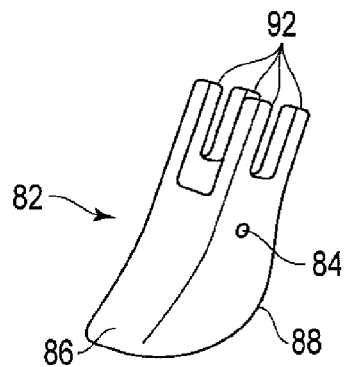
F I G. 4C

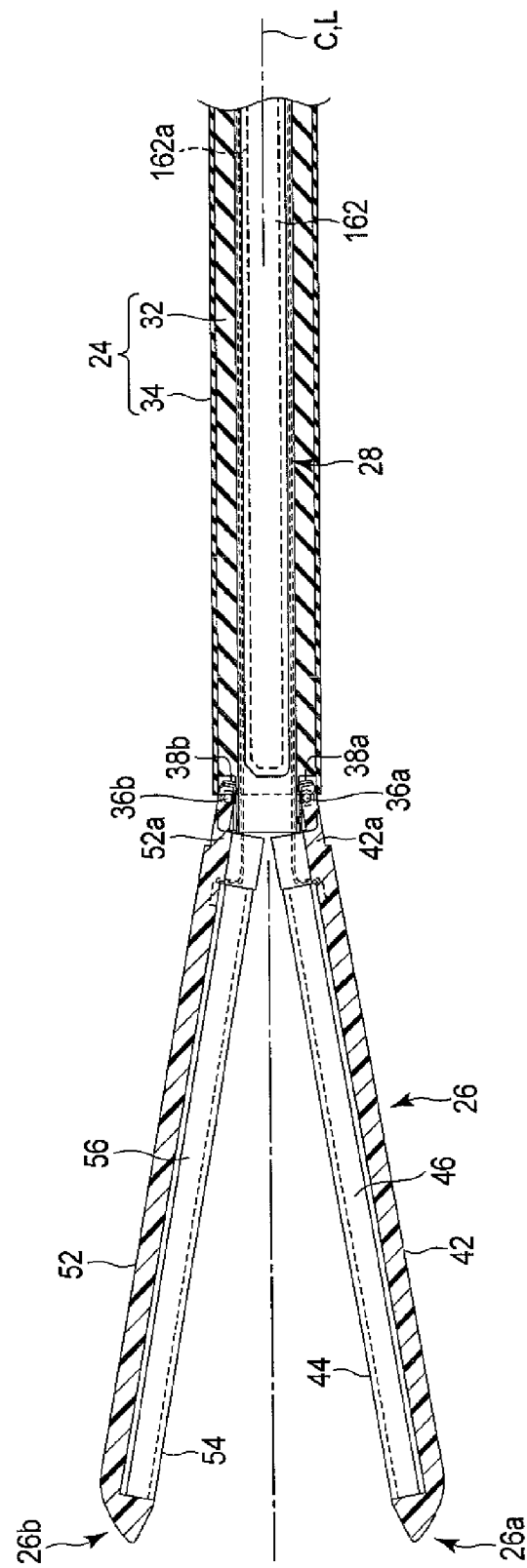
F I G. 7B

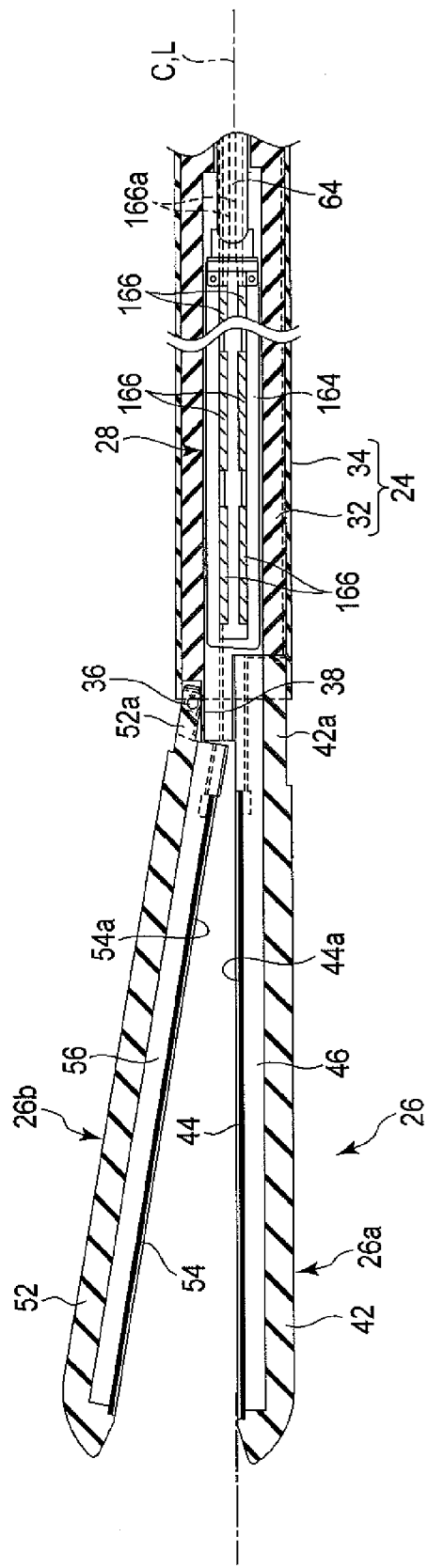
F I G. 8A

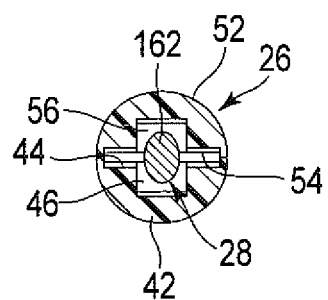
F I G. 9C

HANDLE FOR MEDICAL TREATMENT DEVICE AND MEDICAL TREATMENT DEVICE

CROSS-REFERENCE TO RELATED APPLICATIONS

This is a Continuation Application of PCT Application No. PCT/JP2014/084361, filed Dec. 25, 2014, and based upon and claiming the benefit of priority from prior U.S. Provisional Application No. 61/921,222, filed Dec. 27, 2013, the entire contents of which are incorporated herein by reference.

BACKGROUND OF THE INVENTION

1. Field of the Invention

The present invention relates to a treatment device used for treating a living tissue, and a handle for the treatment device.

2. Description of the Related Art

For example, U.S. Pat. No. 7,156,846 discloses a treatment device having a structure for, while holding a living tissue between a pair of jaws, cutting the held living tissue. The treatment device has a mechanism for maintaining the state where the pair of jaws are relatively closed so as to reduce a user's burden.

For example, when membrane tissue and parenchymal tissue are sequentially treated, the process of closing the pair of jaws and cutting a living tissue immediately after releasing the state where the pair of jaws are closed and advancing the pair of jaws is repeated.

BRIEF SUMMARY OF THE INVENTION

One aspect of a handle according to the present invention includes: a handle main body; a first operation input body provided on the handle main body and configured to rotate in first and second directions to operate a first end effector; an interlock body rotatable relative to the first operation input body; an engaging portion provided in the interlock body and configured to be engaged with the handle main body and to restrict rotation of the first operation input body in the second direction when the first operation input body is rotated in the first direction; and a second operation input body configured to rotate to operate a second end effector, and disengage the engaging portion from the handle main body by pressing the interlock body.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic perspective view showing a medical treatment system according to a first to third embodiments.

FIG. 1B is a schematic view showing a state where a living tissue is treated by a first end effector of a treatment device of the medical treatment system according to the first to third embodiments.

FIG. 2A is a schematic vertical cross-sectional view showing the first end effector in an open state and a second end effector arranged in a shaft of the treatment device of the medical treatment system according to the first embodiment.

FIG. 2B is a schematic vertical cross-sectional view showing the first end effector in a closed state and the second end effector arranged in the shaft of the treatment device of the medical treatment system according to the first embodiment.

FIG. 3A is a schematic side view showing a proximal end of the shaft of the treatment device of the medical treatment system of the first embodiment and a state where a treatment portion is opened by bringing an opening-closing lever farther from a handle.

FIG. 3B is a schematic side view showing the proximal end of the shaft of the treatment device of the medical treatment system of the first embodiment and a state where the treatment portion is closed by bringing the opening-closing lever closer to the handle, and showing a state where the drive lever can be brought closer to and farther from the handle.

FIG. 4A is a schematic view showing a coupling member, a drive rod, and a cutter (second end effector) which move in accordance with the drive lever of the treatment device of the medical treatment system according to the first embodiment.

FIG. 4B is a schematic view showing the coupling member which moves in accordance with the drive lever of the treatment device of the medical treatment system according to the first embodiment.

FIG. 4C is a schematic view showing the drive lever of the treatment device of the medical treatment system according to the first embodiment.

FIG. 7B is a schematic vertical cross-sectional view showing the first and second holding portions in an open state and a cutter (second end effector) arranged in the shaft of the treatment device of the medical treatment system according to the second embodiment.

FIG. 8A is a schematic vertical cross-sectional view showing the first and second holding portions (first end effector) in an open state and a cutter (second end effector) to which a heater is attached and which is arranged in the first and second holding portions through the shaft of the treatment device of the medical treatment system according to a modification of the second embodiment.

FIG. 9C is a schematic transverse cross-sectional view of the treatment device of the medical treatment system according to the modification of the second embodiment taken along line 9C-9C in FIG. 9A.

DETAILED DESCRIPTION OF THE INVENTION

Figure 5A:
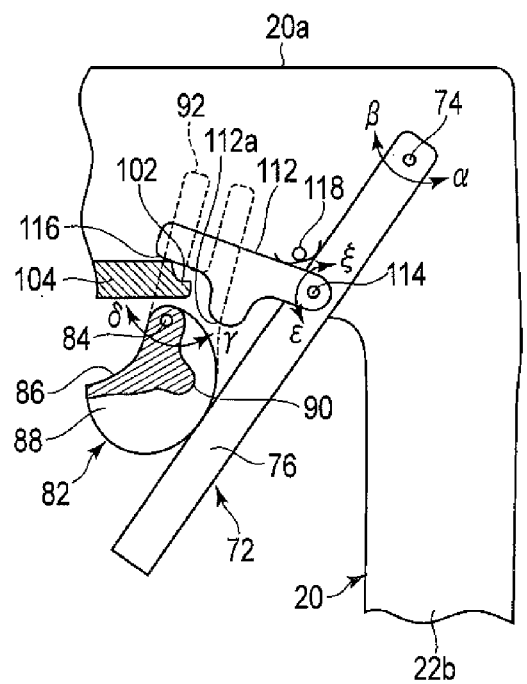
FIG. 5A is a schematic side view showing an operation state of the opening-closing lever, drive lever, and interlock body provided in the handle of the treatment device of the medical treatment system of the first to third embodiments relative to the handle, and a state where the opening-closing lever and drive lever are brought further from the other end of the handle to be opened, and an engaging portion of the interlock body is disengaged from an engaged portion of a handle main body.

Hereinafter, embodiments of the present invention will be described with reference to the drawings.

A first embodiment will be described with reference to FIGS. 1A to 5D.

As shown in FIG. 1A, a medical treatment system 10 according to this embodiment includes a treatment device (medical treatment device) 12 and an energy source (controller) 14. The treatment device 12 will be described by using, as an example, a linear-type surgical treatment device for, for example, performing a treatment through an abdominal wall. The energy source 14 is connected to a foot switch (which may be a hand switch) 16 including a pedal 16a by cable 18b. The treatment device 12 is connected to the energy source 14 by cable 18a.

As shown in FIGS. 1A to 2B, the treatment device 12 includes a handle (handle for a treatment device) 20 supported by an operator, a shaft 24 extending from the handle 20 along a central axis C (longitudinal axis L), a first end effector 26, and a second end effector 28. In this embodiment, by the operator operating the pedal 16a of the foot switch 16, switching between ON and OFF of a supply of energy from the energy source 14 to the first end effector 26 (specifically, first and second energy output portions 44 and 54 to be described later) of the treatment device 12 is performed. When the pedal 16a is pressed, energy is output from the energy source 14 based on the appropriately-set state (state where the energy output amount and energy output timing etc. are controlled) of the energy source 14. When the pedal 16a is released, the output of energy is forcibly stopped.

As shown in FIGS. 2A and 2B, the shaft 24 includes an inner cylinder 32 and an outer cylinder 34 slidably provided outside the inner cylinder 32. As shown in FIGS. 3A and 3B, the inner cylinder 32 is fixed to the handle 20 at its proximal end. The outer cylinder 34 is slidable in the axial direction of the inner cylinder 32.

As shown in FIGS. 1A, 2A, and 2B, the first end effector 26 is provided at a distal end of the shaft 24. The first end effector 26 includes a first holding portion 26a and a second holding portion 26b. The first holding portion 26a includes a first jaw 42, a first energy output portion 44 including a first holding surface 44a, and a guide groove (second end effector placement portion) 46 to which a cutter (movable body) 62 including the first jaw 42 and the first energy output portion 44, which is a second end effector 28 and will be described later, is guided. The second holding portion 26b includes a second jaw 52, a second energy output portion 54 including a second holding surface 54a, and a guide groove (second end effector placement portion) 56 to which a cutter 62 including the second jaw 52 and the second energy output portion 54, which is a second end effector 28 and will be described later, is guided. The first and second jaws 42 and 52 can be brought relatively close to and far from each other. The first energy output portion 44 is provided on the first jaw 42, the second energy output portion 54 is provided on the second jaw 52, and the holding surfaces 44a and 54a of the first and second energy output portions 44 and 54 are opposed to each other. The second jaw 52 and the second energy output portion 54 is relatively movable between an open state where the second jaw 52 and the second energy output portion 54 are far from the first jaw 42 and the first energy output portion 44, and a closed state where the second jaw 52 and the second energy output portion 54 are close to the first jaw 42 and the first energy output portion 44. The first and second jaws 42 and 52 each preferably have insulation properties over their entirety. The first and second energy output portions 44 and 54 are each, for example, a high frequency electrode or a heater, and connected to the energy source 14. Thus, a living tissue arranged between the holding surfaces 44a and 54a of the first and second energy output portions 44 and 54 is treated by heat energy.

The first jaw 42 is fixed to the distal end of the inner cylinder 32 of the shaft 24 at a proximal portion 42a of the first jaw 42. The second jaw 52 is supported by a support pin 36 rotatably provided in a direction orthogonal to the axial direction of the shaft 24 in the distal end of the inner cylinder 32 of the shaft 24 at a proximal portion 52a of the second jaw 52. The second jaw 52 can be opened and closed relative to the first jaw 42 by rotating around the axis of the support pin 36. The second jaw 52 is pushed by an elastic member 38 such as a leaf spring so that the second jaw 52 opens relative to the first jaw 42.

By sliding the outer cylinder 34 relative to the inner cylinder 32, the proximal portions 42a and 52a of the first and second jaws 42 and 52 can be covered by the distal end of the outer cylinder 34. In this state, the second jaw 52 resists the pushing force of the elastic member 38 and closes relative to the first jaw 42, as shown in FIGS. 2A and 2B. In contrast, as the outer cylinder 34 is slid to the proximal end side of the inner cylinder 32 from the state where the proximal portions 42a and 52a of the first and second jaws 42 and 52 are covered by the distal end of the outer cylinder 34, the second jaw 52 opens relative to the first jaw 42 by the pushing force of the elastic member 38, as shown in FIG. 2A.

The second end effector 28 includes a sheet-shaped cutter (treatment aid) 62. Inside the inner cylinder 32 of the shaft 24, a drive rod 64 is provided movably in its axial direction.

A blade 62a is formed at a distal end of the cutter 62, and a distal end of the drive rod 64 is fixed to a proximal end of the cutter 62. A long groove 62b is formed between the distal end and the proximal end of the cutter 62. In the long groove 62b, a movement restriction pin 66 extending in a direction orthogonal to the axial direction of the shaft 24 is fixed to the inner cylinder 32 of the shaft 24. A locking part 62c for locking the movement restriction pin 66 and controlling movement of the cutter 62 is formed at at least three points: one end, the other end, and between one end and the other end of the long groove 62b of the cutter 62. Therefore, when a drive lever 82 to be described later is operated, the cutter 62 is moved along the movement restriction pin 66 via the drive rod 64. The cutter 62 moves straight, and is placed in the guide grooves 46 and 56.

To place the cutter 62 in the guide grooves 46 and 56, the long groove 62b and the movement restriction pin 66 are not always needed.

The handle 20 includes a handle main body 20a, and is formed into a shape easily held by an operator, which is, for example, an approximate L-shape in this embodiment. The handle main body 20a includes one end (distal end) 22a on which the proximal end of the shaft 24 is placed, and the other end 22b which is a grip portion held by an operator. One end (distal end) 22a of the handle main body 20a is provided with the proximal end of the shaft 24. The above-mentioned cable 18a extends from the proximal end of the handle main body 20a, for example, approximately coaxially arranged with the shaft 24.

The other end 22b of the handle main body 20a is the grip portion held by an operator. Between one end 22a and the other end 22b of the handle main body 20a, a treatment portion opening-closing lever (first operation input body) 72 is provided parallel to the other end 22b. In this embodiment, the treatment portion opening-closing lever 72 is provided in front of the other end 22b of the handle main body 20a. The opening-closing lever 72 receives an input of an operation for causing the first end effector 26 to operate on a living tissue to be treated. Namely, the opening-closing lever 72 is used to operate the first end effector 26.

The treatment portion opening-closing lever 72 is coupled to the proximal end of the outer cylinder 34 (see FIGS. 2A and 2B) of the shaft 24 in approximately the center of the handle main body 20a. When the treatment portion opening-closing lever 72 is brought closer to or farther from the other end 22b of the handle main body 20a, the outer cylinder 34 moves in its axial direction.

The treatment portion opening-closing lever 72 includes a pivot shaft 74, an operation portion 76, and a pair of lugs 78. The treatment portion opening-closing lever 72 can pivot in a first direction α (in which the handle main body 20a approaches the other end 22b) and a second direction β (in which the handle main body 20a is separated from the other end 22b), which are shown in FIG. 3A, in the handle main body 20a by use of the pivot shaft 74. The operation portion 76 protrudes outside from a bottom end of the handle main body 20a, and is provided in front of the other end 22b of the handle main body 20a. Thus, the operation portion 76 can be brought farther from (see FIG. 3A) and closer to (see FIG. 3B) the other end 22b of the handle main body 20a.

The pair of lugs 87 are provided at an upper end of the treatment portion opening-closing lever 72, formed into an approximate Y-shape to support the proximal end of the outer cylinder 34, and engaged with a pin 34a provided at the proximal end of the outer cylinder 34 of the shaft 24 in the handle main body 20a. The pin 34a extends in an outer direction orthogonal to the central axis C of the outer cylinder 34. Thus, the pin 34a provided at the proximal end of the outer cylinder 34 is supported movably relative to the lugs 78 at the upper end of the treatment portion opening-closing lever 72. Therefore, the outer cylinder 34 can be moved relative to the handle main body 20a and the inner cylinder 32 by an operation of the operation portion 76 of the treatment portion opening-closing lever 72.

The treatment portion opening-closing lever 72 is coupled to the proximal end of the outer cylinder 34 (to be described later) of the shaft 24 in approximately the center of the handle main body 20a. Thus, when the treatment portion opening-closing lever 72 is brought closer to the other end 22b of the handle main body 20a, the outer cylinder 34 (to be described later) of the shaft 24 moves forward in its axial direction relative to the handle main body 20a. In contrast, when the treatment portion opening-closing lever 72 is brought farther from the other end 22b of the handle main body 20a, the outer cylinder 34 moves backward in its axial direction relative to the handle main body 20a.

As shown in FIGS. 1A, 3A, and 3B, the handle main body 20a is provided with a drive lever (second operation input body) 82, which moves the cutter 62 serving as the second end effector 28, in front of the treatment portion opening-closing lever (first operation input body) 72 (at a position closer to the first end effector 26 than the treatment portion opening-closing lever 72). Namely, the drive lever 82 is supported at a position closer to one end 22a of the handle main body 20a than the opening-closing lever 72.

The cutter drive lever 82 is coupled to the proximal end of the drive rod 64 provided within the shaft 24 in approximately the center of the handle main body 20a. When the cutter drive lever 82 is brought closer to or farther from the other end 22b of the handle 20, the drive rod 64 and the cutter 62 move in its axial direction. The drive lever 82 receives an input of an operation to actuate the second end effector 28 different from the first end effector 26 to operate on a living tissue and to disengage the interlock body 112 (to be described later) engaged with the handle main body 20a. Namely, the drive lever 82 is used to operate the second end effector 28.

As shown in FIGS. 3A to 4C, the drive lever 82 includes a pivot shaft 84, an operation portion 86 on which an index finger or a middle finger can be caught, a pair of contact surfaces (first contact portion) 88 brought into contact with the opening-closing lever 72, a projection (second contact portion) 90 brought into contact with a projection 112a of the interlock body 112 to be described later, and a lug 92. The drive lever 82 can pivot in a first direction γ (in which the handle main body 20a approaches the other end 22b) and a second direction δ (in which the handle main body 20a is separated from the other end 22b), which are shown in FIG. 3A, by the pivot shaft 84 provided in the handle main body 20a. The operation portion 86 of the drive lever 82 protrudes outside from a bottom end of the handle main body 20a, and is provided in front of the other end 22b of the handle main body 20a. Thus, the operation portion 86 of the drive lever 82 can be brought closer to (see the broken line in FIG. 3B) and farther from (see the solid line in FIG. 3B) the other end 22b of the handle main body 20a. The lug 92 is at an upper end of the drive lever 82, and is engaged with a pin 98 provided on a coupling member 94 fixed to the proximal end of the drive rod 64 within the handle main body 20a.

As shown in FIG. 4B, the coupling member 94 includes: a main body 96 having a through hole 96a at the proximal end of the drive rod 64; and a pin 98 extending in an outer direction orthogonal to the central axis C of the through hole 96a. The coupling member 94 is fixed to the proximal end of the drive rod 64. As shown in FIG. 4A, the pin 98 extends in a direction orthogonal to the plane surface of the cutter 62, and is engaged with the lug 92 provided at the upper end of the drive lever 82.

Thus, the operation portion 86 of the drive lever 82 can be brought closer to and farther from the other end 22b of the handle 20. As the operation portion 86 of the drive lever 82 is operated and the drive rod 64 is moved forward via the coupling member 94, the cutter 62, i.e., the second end effector 28, moves forward. As the drive rod 94 is moved backward via the coupling member 94, the cutter 62, i.e., the second end effector 28, moves backward. At this time, the cutter 62, i.e., the second end effector 28, moves along the first and second guide grooves (flow path, fluid discharge groove) 46 and 56. In particular, when the distal end of the cutter 62 moves most forward, the distal end (blade 62a) of the cutter 62 is located slightly on the proximal end side relative to the distal ends of the guide grooves 46 and 56. When the distal end of the cutter 62 moves most backward, the distal end of the cutter 62 is located inward of the distal end of the inner cylinder 32 or at a position of the proximal ends of the guide grooves 46 and 56 so as not to come into contact with the living tissue.

As shown in FIGS. 5A to 5D, the handle main body 20a includes a support portion 104 including an engaged portion 102 which the engaging portion 116 of the interlock body 112 to be described later is mounted on and into which the engaging portion 116 is engaged with or fitted. The engaged portion 102 has a vertical cross-section having an approximate L-shape. At the engaged portion 102, the inner side of the handle main body 20a is concaved, and the bottom end side (outer side) is convexed.

On the opening-closing operation lever 72, the interlock body 112 which moves in accordance with the opening-closing operation lever 72 is supported by a rotational shaft 114. The rotational shaft 114 is supported by the proximal end of the interlock body 112. The interlock body 112 can be rotated by the rotational shaft 114 in a first direction ε and a second direction ζ. The interlock body 112 moves in accordance with an input of an operation to the opening-closing lever (first operation input body) 72. As the opening-closing lever 72 rotates in the first direction α, the interlock body 112 rotates in the first direction ε or second direction ζ, and restricts rotation of the opening-closing lever 72 in the second direction β when the interlock body 112 is engaged with the handle main body 20a.

The interlock body 112 has, at its distal end, an engaging portion 116 that can be engaged with the engaged portion 102 of the handle main body 20a. An elastic body 118 which pushes the engaging portion 116 of the interlock body 112 to the engaged portion 102 of the handle main body 20a is provided between the opening-closing, operation lever 72 and the interlock body 112.

Figure 5B:
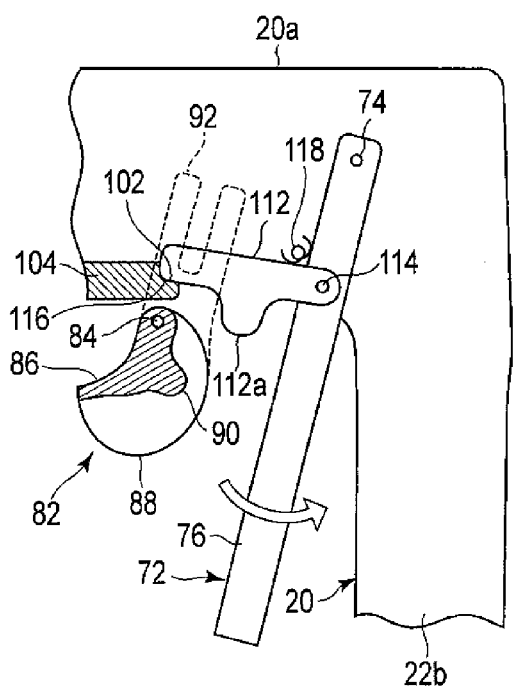
FIG. 5B is a schematic side view showing an operation state of the opening-closing lever, drive lever, and interlock body provided in the handle of the treatment device of the medical treatment system of the first to third embodiments relative to the handle, and a state where the opening-closing lever is brought closer to the other end of the handle to be opened while keeping the drive lever far from the other end of the handle, and the engaging portion of the interlock body is engaged with the engaged portion of the handle main body.
Figure 5C:
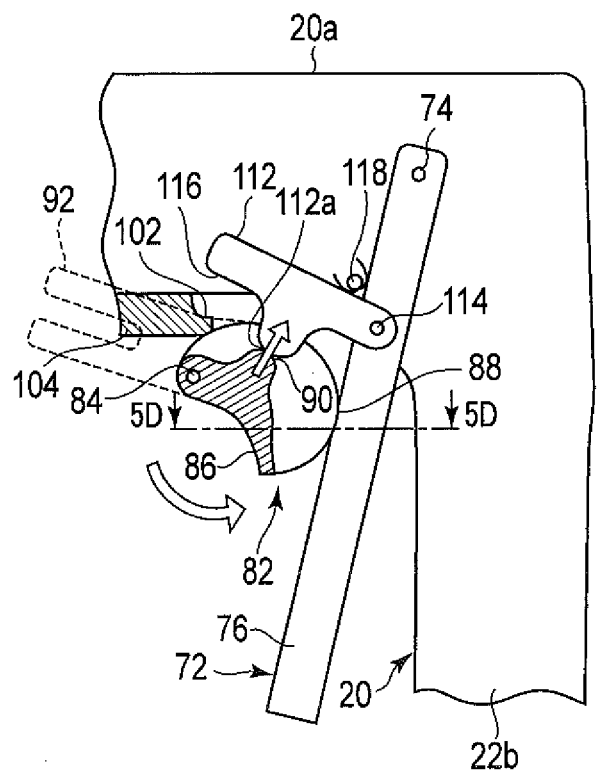
FIG. 5C is a schematic side view showing an operation state of the opening-closing lever, drive lever, and interlock body provided in the handle of the treatment device of the medical treatment system of the first to third embodiments relative to the handle, and a state where the drive lever is brought closer to the other end of the handle to be closed while keeping the opening-closing lever close to the other end of the handle to be closed, and a contact surface of the drive lever is brought into contact with the opening-closing lever immediately after the engaging portion of the interlock body is disengaged from the engaged portion of the handle main body.
Figure 5D:
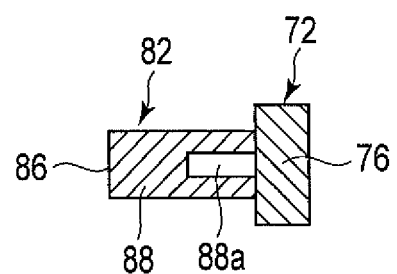
FIG. 5D is a transverse cross-sectional view of the opening-closing lever and the drive lever of the treatment device of the medical treatment system according to the first embodiment taken along line 5D-5D in FIG. 5C.

As shown in FIGS. 5A-5C, the interlock body 112 includes a projection 112a which projects toward the bottom end of the handle main body 20a. In other words, the interlock body 112 includes the projection 112a which projects toward the drive lever 82 to come into contact with the projection 90 of the drive lever (second operation input body) 82.

As shown in FIGS. 5A to 5D, the projection 90 of the drive lever 82 is at a position closer to the operation portion 86 than proximal end side edges of the pair of contact surfaces 88 and is formed between the pair of contact surfaces 88. Therefore, a space 88a is formed between projection 90 and the contact surfaces 88. As shown in FIG. 5C, the interlock body 112 does not come into contact with the pair of contact surfaces 88 of the drive lever 82, and the projection 90 of the cutter drive lever 82 comes into contact with the projection 112a of the interlock body 112. When the drive lever 82 is rotated in the first direction γ with the interlock body 112 engaged with the handle main body 20a, the drive lever 82 comes into contact with the interlock body 112 before coming into contact with the opening-closing lever 72. The contact surfaces 88 are formed as, for example, a planer cam. The contact position between the contact surfaces 88 of the drive lever 82 and the operation portion 76 of the opening-closing lever 72 shown in FIG. 5A is closer to the pivot shaft 84 of the drive lever 82 than the contact position between the contact surfaces 88 of the drive lever 82 and the operation portion 76 of the opening-closing lever 72 shown in FIG. 5C. The contact surfaces 88 formed as a planer cam are controlled, when the opening-closing lever 72 at the position shown in FIG. 5C is returned to the position shown in FIG. 5A, to move the blade 62a of the cutter 62 to the inside of the shaft 24 while maintaining the state where the first and second holding portions 26a and 26b are closed as much as possible. Therefore, it is possible to prevent the cutter 62 from being provided between a living tissue while not holding the living tissue. By appropriately setting the shapes of the contact surfaces 88, the positional relationship between the first end effector 26 and the second end effector 28 can be appropriately controlled.

Next, an advantage of the medical treatment system 10 according to this embodiment will be described with reference to FIGS. 5A to 5C.

From the state where the opening-closing lever 72 and the cutter drive lever 82 are at the positions shown in FIG. 5A, the operation portion 76 of the opening-closing lever 72 is rotated in the first direction α to bring the operation portion 76 of the opening-closing lever 72 closer to the other end 22b of the handle main body 20a. At this time, the interlock body 112 is pushed to the support portion 104 of the handle main body 20a by the elastic body 118. Thus, the engaging portion 116 of the interlock body 112 is brought closer to the engaged portion 102 of the support portion 104 while keeping contact with the support portion 104 of the handle main body 20a. Namely, in accordance with the movement of the opening-closing lever 72, the engaging portion 116 of the interlock body 112 supported by the rotational shaft 114 is brought closer to the engaged portion 102 of the handle main body 20a. At this time, the interlock body 112 may be moved in the second direction ζ relative to the opening-closing lever 72 by the rotational shaft 114. As shown in FIG. 5B, the engaging portion 116 of the interlock body 112 is engaged with or fitted into the engaged portion 102 of the handle main body 20a. At this time, the interlock body 112 is rotated in the first direction ε relative to the opening-closing lever 72 by the rotational shaft 114.

The elastic body 118 pushes the interlock body 112 to maintain the state where the engaging portion 116 of the interlock body 112 is engaged with the engaged portion 102. Thus, rotation of the opening-closing lever 72 in the second direction β is restricted.

When the opening-closing lever 72 rotates in the first direction α, the outer cylinder 34 moves forward relative to the inner cylinder 32, and the second jaw 52 closes relative to the first jaw 42. Namely, when the opening-closing lever 72 is rotated in the first direction α, the first end effector 26 can be operated. Therefore, the holding surfaces 44a and 54a of the energy output portions 44 and 54 can hold a living tissue. When the pedal 16a of the foot switch 16 is pressed in this state, the living tissue between the energy output portions 44 and 54 is treated by heat energy from the energy output portions 44 and 54, as shown in FIG. 1B.

After such a treatment, the drive lever 82 is rotated in the first direction γ and brought closer to the opening-closing lever 72. As shown in FIG. 5C, the cutter drive lever 82 comes into contact with the interlock body 112 before coming into contact with the opening-closing lever 72. More specifically, the projection 90 of the drive lever 82 is brought into contact with the projection 112a of the interlock body 112. Then, the interlock body 112 is flipped up in the second direction ζ around the rotational shaft 114 against the pushing force of the elastic body 118 to cancel the state in which the engaging portion 116 is engaged with the engaged portion 102. The pair of contact portions 88 of the drive lever 82 are brought into contact with the opening-closing lever 72.

Accordingly, when the pair of contact portions 88 of the drive lever 82 are brought into contact with the opening-closing lever 72, the interlock body 112 has been rotated in the second direction ζ around the rotational shaft 114, and the state in which the engaging portion 116 is engaged with the engaged portion 102 has been canceled.

When the drive lever 82 is rotated in the first direction γ, the cutter 62, i.e., the second end effector 28, moves forward via the drive rod 64, as shown in FIG. 4A. Therefore, the living tissue treated by using heat energy can be incised by the blade 62a of the cutter 62.

Since the interlock body 112 is flipped up by the drive lever 82 in the second direction ζ around the rotational shaft 114 toward the inside of the handle main body 20a, the engaging portion 116 of the interlock body 112 is not engaged with the engaged portion 102 of the handle main body 20a. Thus, the opening-closing lever 72 can be rotated in the second direction β. When the opening-closing lever 72 is rotated in the second direction β, the drive lever 82 in contact with the opening-closing lever 72 is also rotated in the second direction δ. Then, the engaging portion 116 of the interlock body 112, which moves in accordance with the opening-closing lever 72, is brought farther from the engaged portion 102 of the support portion 104 of the handle main body 20a.

Accordingly, the blade 62a of the cutter 62 is drawn and removed from the living tissue, and the second jaw 52 opens relative to the first jaw 42. Consequently, the second end effector 28 is operated, and the first end effector 26 is operated.

The first and second jaws 42 and 52 in an open state are moved forward to the living tissue, and closed by bringing the opening-closing lever 72 closer to the other end 22b of the handle main body 20a, and the living tissue is treated by heat energy by pressing the pedal 16a of the foot switch 16. Then, the drive lever 82 is operated to incise the living tissue with the cutter 62. Thereafter, the cutter 62 is drawn into the shaft 24 while rotating the opening-closing lever 72 in the second direction β. By sequentially repeating these operations, not only the living tissue between the energy output portions 44 and 54, but also a living tissue in front thereof can be incised while sequentially joining the living tissue.

The operation of the above-described handle 20 will be schematically described. In the handle main body 20a held by an operator, the first operation input body 72 rotatable in the first and second directions α and β with respect to the handle main body 20a is rotated in the first direction α to operate the first end effector 26 to perform the function of the first end effector 26 on a living tissue. Next, the interlock body 112 rotatable in the third and fourth directions ε and ζ in accordance with the rotation of the first operation input body 72 is appropriately rotated to be engaged with the handle main body 20a to operate the first end effector 26 to maintain the state of performing the function on the living tissue. With the state maintained where the first end effector 26 is operated, the second operation input body 82 rotatable in the fifth and sixth directions γ and δ is rotated in the fifth direction γ to operate the second end effector 28 to perform the function of the second end effector 28 on the living tissue. In accordance with the rotation of the second operation input body 82 in the fifth direction γ, the interlock body 112 is rotated in the fourth direction ζ to disengage the interlock body 112 from the handle main body 20a. Finally, in accordance with the rotation of the first operation input body 72 in the second direction β, performance of the function of the first end effector 26 is stopped, and the second operation input body 82 is rotated in the sixth direction δ to stop performance of the function of the second end effector 28.

As described above, this embodiment performs the following advantage.

After rotating, in the first direction α, the opening-closing lever 72 rotatably supported relative to the handle main body 20a to hold the living tissue with the first and second holding portions 26a and 26b, a treatment of applying heat energy to the living tissue held between the energy output portions 44 and 54 can be performed by pressing the pedal 16a of the foot switch 16. By operating the drive lever 82 in this state, the state in which the interlock body 112, which moves in accordance with the opening-closing lever 72, is engaged with the handle main body 20a can be canceled, and the living tissue can be incised by the cutter 62.

Accordingly, a series (one cycle) of operations of performing a treatment (with the first end effector 26) by outputting energy from the energy output portions 44 and 54 to the living tissue held between the pair of holding portions 26a and 26b, performing a treatment (with the second end effector 28) of cutting the treated living tissue with the cutter 62, and drawing the cutter 62 while releasing holding of the living tissue between the pair of holding portions 26a and 26b, can be completed by an operation of the opening-closing operation lever 72 and the drive lever 82 by one hand of an operator, that is, can be performed without an extra operation.

Since the interlock body 112 engaged with the handle main body 20a can be disengaged by an operation of the drive lever 82, this embodiment can make the interlock body 112 move in accordance with not only the opening-closing lever 72, but also the drive lever 82. Therefore, for example, the trouble of disengaging the opening-closing lever 72 engaged with the handle main body 20a after moving the drive lever 82 forward, incising a living tissue, and moving the drive lever 82 backward, can be reduced. Consequently, the series of operations of the treatment on the living tissue using energy and cutting of the living tissue can be efficiently performed, and the efficiency in the operation of similarly treating and cutting a living tissue in front of the treated and cut living tissue can be greatly improved.

When the drive lever 82 is rotated in the first direction γ with the interlock body 112 engaged with the handle main body 20a, both or one of the projections 90 and 112a are not always necessary as long as the drive lever 82 comes into contact with the interlock body 112 before the cutter drive lever 82 comes into contact with the opening-closing lever 72.

Figure 6A:
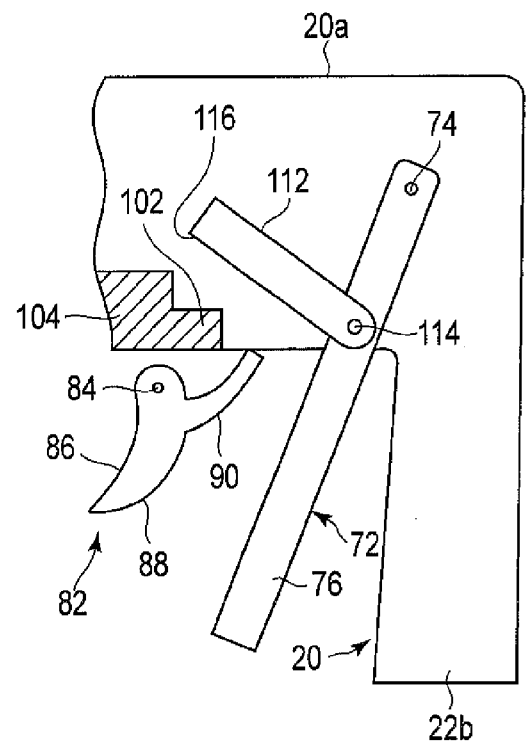
FIG. 6A is a schematic side view showing a modification of the opening-closing lever, drive lever, and interlock body provided in the handle of the treatment device of the medical treatment system of the first to third embodiments, and showing a case where a projection is formed on the drive lever, and no projection is formed on the interlock body.

FIG. 6A shows an example in which a projection 90 is formed on the drive lever 82, and no projection is formed on the interlock body 112.

Figure 6B:
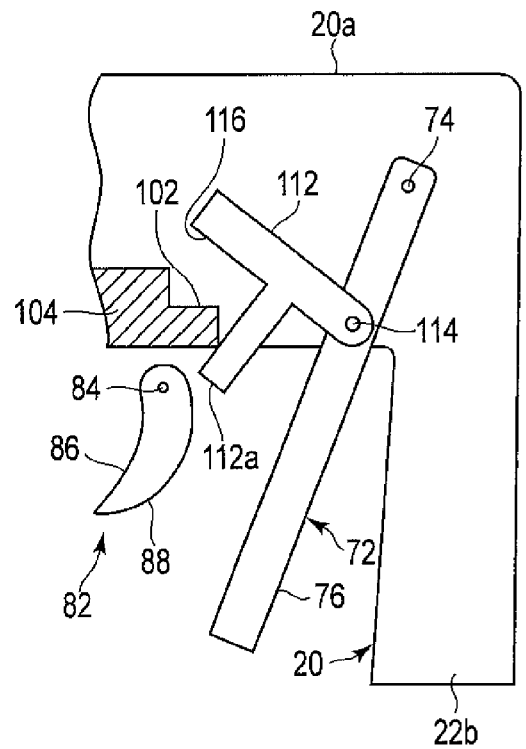
FIG. 6B is a schematic side view showing a modification of the opening-closing lever, drive lever, and interlock body provided in the handle of the treatment device of the medical treatment system of the first to third embodiments, and showing a case where no projection is formed on the drive lever, and a projection is formed on the interlock body.

FIG. 6B shows an example in which no projection is formed on the drive lever 82, and a projection 112a is formed on the interlock body 112.

Figure 6C:
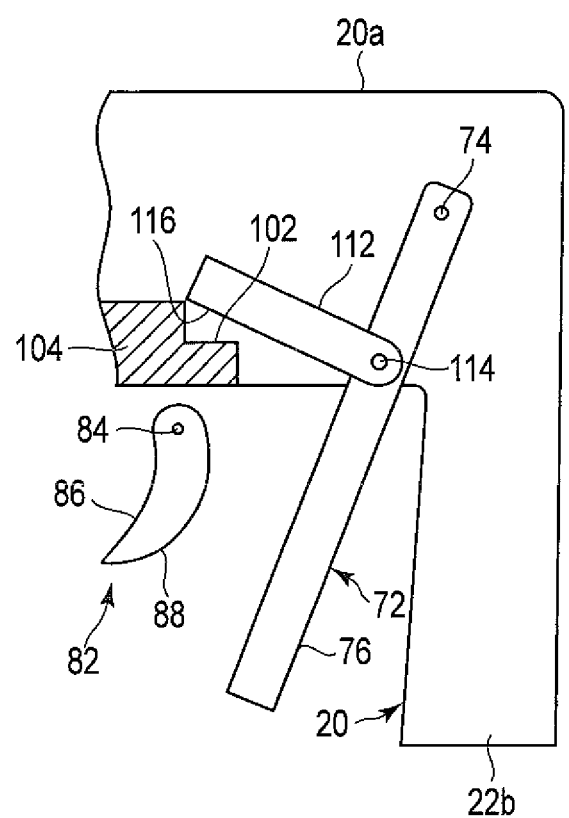
FIG. 6C is a schematic side view showing a modification of the opening-closing lever, drive lever, and interlock body provided in the handle of the treatment device of the medical treatment system of the first to third embodiments, and showing a case where no projection is formed on both of the drive lever and the interlock body.

FIG. 6C shows an example in which no projection is formed on both the drive lever 82 and the interlock body 112.

FIGS. 6A to 6C show that the above-described elastic member 118 (see FIGS. 5A to 5C) are not always necessary between the treatment portion opening-closing lever 72 and the interlock body 112.

Next, the second embodiment will be described with reference to FIGS. 7A to 7C. This embodiment is a modification of the first embodiment. Elements which are the same as those described in the first embodiment or which have the same functions as those described in the first embodiment will be assigned with the same reference symbols, and detailed descriptions thereof will be omitted.

Figure 7A:
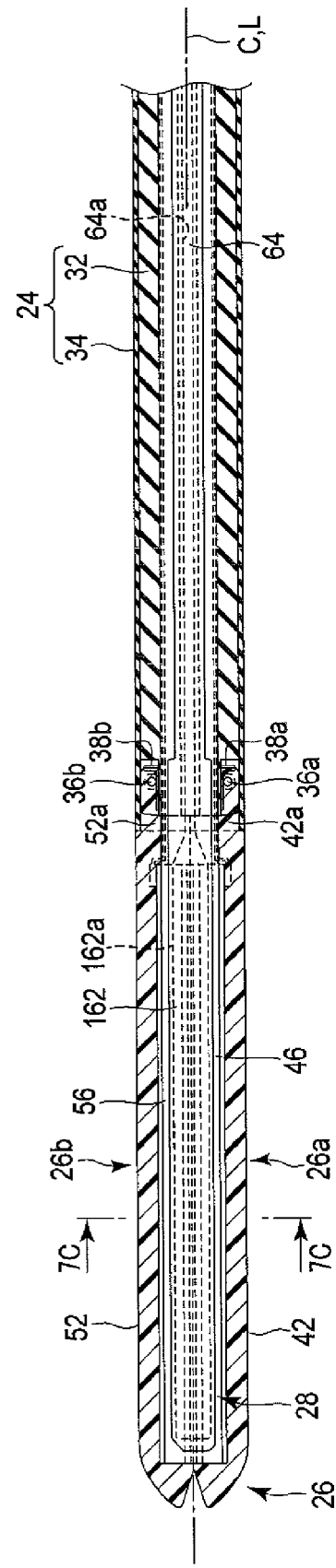
FIG. 7A is a schematic vertical cross-sectional view showing the first and second holding portions (first end effector) in a closed state and a cutter (second end effector) arranged in the first and second holding portions through the shaft of the treatment device of the medical treatment system according to the first embodiment.
Figure 7C:
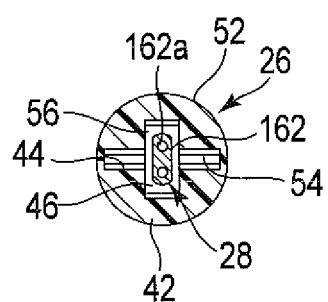
FIG. 7C is a schematic transverse cross-sectional view of the treatment device of the medical treatment system according to the second embodiment taken along line 7C-7C in FIG. 7A.

As shown in FIGS. 7A and 7B, the first end effector 26 according to the present embodiment includes holding portions 26a and 26b which are both movable. Instead of the cutter (cold cutter) 62, another cutter (movable body) 162 is used as the second end effector 28. The cutter 162 includes a heat transfer line 162a which functions as a heat resistance for converting a current flowing therein into heat. The heat transfer line 162a is connected to the energy source 14 through a pipe line 64a within the drive rod 64. When a current flows from the energy source 14 to the heat transfer line 162a of the cutter (hot cutter) 162, a living tissue can be incised by heat energy easier than the cutter (cold cutter) 62 described in the first embodiment.

The proximal portions 42a and 52a of the first and second jaws 42 and 52 are both supported by support pins 36a and 36b provided in the distal end portion of the inner cylinder 32 in a direction orthogonal to the axial direction of the shaft 24 rotatably relative to the distal end portion of the inner cylinder 32 of the shaft 24. The support pins 36a and 36b are provided in the distal end portion of the inner cylinder 32 to be parallel to each other. The first and second jaws 42 and 52 can be opened and closed by the proximal portions 42a and 52a rotating around the axes of the support pins 36a and 36b. As shown in FIGS. 7A and 7B, elastic members 38a and 38b are provided on the outer peripherals of the support pins 36a and 36b provided in the distal end portions of the inner cylinder 32. Thus, the first and second jaws 42 and 52 are pushed in their respective opening directions.

When the distal end of the outer cylinder 34 is moved farther from an operator (forward) by an operation of the opening-closing lever 72, a force which closes the proximal portions 42a and 52a is applied at the distal end of the outer cylinder 34. Consequently, the first and second jaws 42 and 52 close against the pushing force of the elastic members 38a and 38b. When the distal end of the outer cylinder 34 is moved closer to an operator (backward) by an operation of the opening-closing lever 72, a force which closes the proximal portions 42a and 52a by the distal end of the outer cylinder 34 is lost and, namely, the first and second jaws 42 and 52 are opened by the pushing force of the elastic members 38a and 38b.

In this embodiment, the drive lever 82 described in the first embodiment functions to move the cutter 162.

In this embodiment, switching between ON and OFF of energy supply from the energy source 14 to the first end effector 26 (more specifically, first and second energy output portions 44 and 54 to be described later) of the treatment device 12 is performed, and switching the supply of energy between ON and OFF for passing a current to the second end effector 28 (more specifically, the cutter 162) is performed.

An advantage of the medical treatment system 10 according to this embodiment will be described. What is described in the first embodiment will be omitted as appropriate.

When the operation portion 76 of the opening-closing lever 72 is brought closer to the other end 22b of the handle main body 20a, the engaging portion 116 of the interlock body 112 is engaged with the engaged portion 102 of the handle main body 20a, as shown in FIG. 5B. At this time, rotation of the opening-closing lever 72 in the second direction β is restricted.

When the opening-closing lever 72 rotates in the first direction α, the outer cylinder 34 moves forward relative to the inner cylinder 32, and the first and second holding portions 26a and 26b close. Namely, when the opening-closing lever 72 rotates in the first direction α, the first end effector 26 actuates. Therefore, the holding surfaces 44a and 54a of the energy output portions 44 and 54 can hold a living tissue. When the pedal 16a of the foot switch 16 is pressed in this state, the living tissue between the energy output portions 44 and 54 is treated by heat energy.

After such a treatment, the drive lever 82 is rotated in the first direction γ and brought closer to the opening-closing lever 72, thereby disengaging the engaging portion 116 of the interlock body 112 from the engaged portion 102 of the handle main body 20a. The pair of contact portions 88 of the drive lever 82 are brought into contact with the opening-closing-lever 72.

When the drive lever 82 is rotated in the first direction γ, the cutter 162 moves forward as shown in FIG. 4A. Namely, when the drive lever 82 rotates in the first direction α, the second end effector 28 operates. Therefore, a living tissue treated by using heat energy can be coagulated and incised with the cutter 162 by further using heat energy.

When the opening-closing lever 72 is rotated in the second direction β, the drive lever 82 in contact with the opening-closing lever 72 is also rotated in the second direction δ. The engaging portion 116 of the interlock body 112, which moves in accordance with the opening-closing lever 72, is brought farther from the engaged portion 102 of the handle main body 20a.

Accordingly, the cutter 162 is drawn and removed from the living tissue, and the first and second holding portions 26a and 26b open. The first and second holding portions 26a and 26b in an open state are moved forward to the living tissue, and the pedal 16a of the foot switch 16 is pressed with the opening-closing lever 72 close to the other end 22b of the handle main body 20a, and then the drive lever 82 is operated to treat the living tissue by ultrasonic energy. Thereafter, the cutter 162 is drawn into the shaft 24 while rotating the opening-closing lever 72 in the second direction β. By sequentially repeating those operations, not only the living tissue between the energy output portions 44 and 54, but also a living tissue in front thereof can be incised while sequentially joining the living tissue.

Figure 8B:
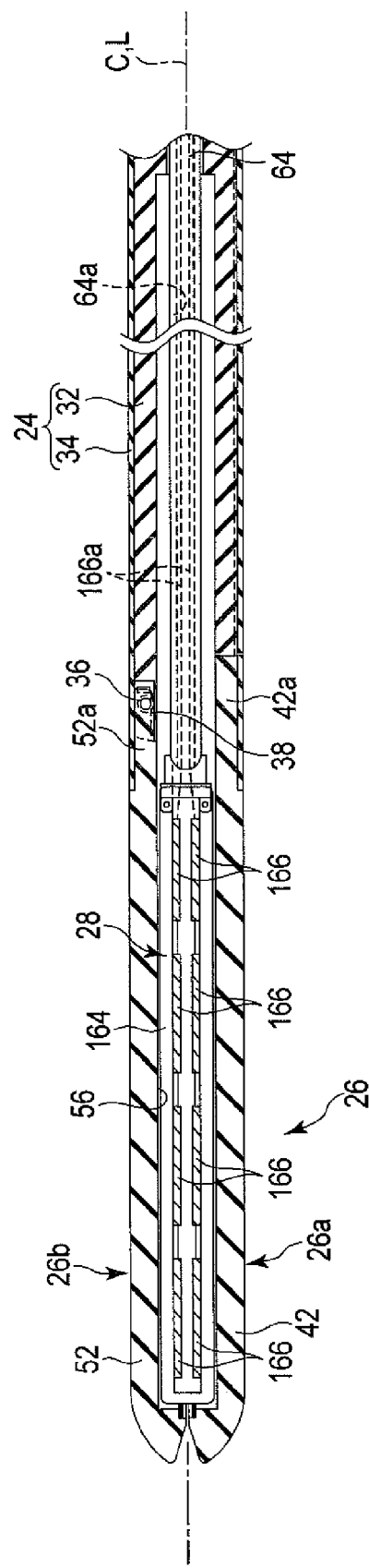
FIG. 8B is a schematic vertical cross-sectional view showing the first and second holding portions (first end effector) in a closed state and a cutter (second end effector) to which a heater is attached and which is arranged in the first and second holding portions of the treatment device of the medical treatment system according to a modification of the second embodiment.

As shown in FIGS. 8A and 8B, it is preferable that a plurality of heaters 166 is provided with the cutter 164. Namely, it is favorable that the second end effector 28 includes the cutter 164 and heaters 166. The heaters 166 may be separately provided in the longitudinal direction, or may be integrated as appropriate. The heaters 166 are connected to the energy source 14 via a current-carrying line 166a. As power is supplied to the heaters 166 through the current-carrying line 166a provided inside the pipe line 64a within the drive rod 64, the heaters 166 generate heat, and transfer the heat to the cutter 164. When a current flows from the energy source 14 to the current-carrying line 166a of the cutter (hot cutter) 164, the living tissue can be incised by heat energy easier than the cutter (cold cutter) 62 described in the first embodiment. Cutter 164 operates in a similar manner to cutter 162.

Figure 9A:
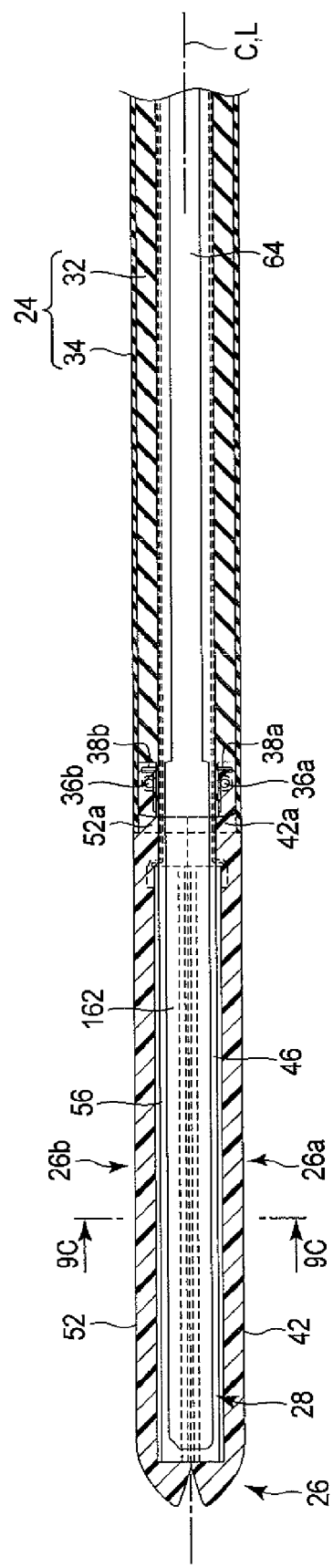
FIG. 9A is a schematic vertical cross-sectional view showing the first and second holding portions (first end effector) in a closed state and an ultrasonic probe (second end effector) arranged in the first and second holding portions through the shaft of the treatment device of the medical treatment system according to a modification of the second embodiment.
Figure 9B:
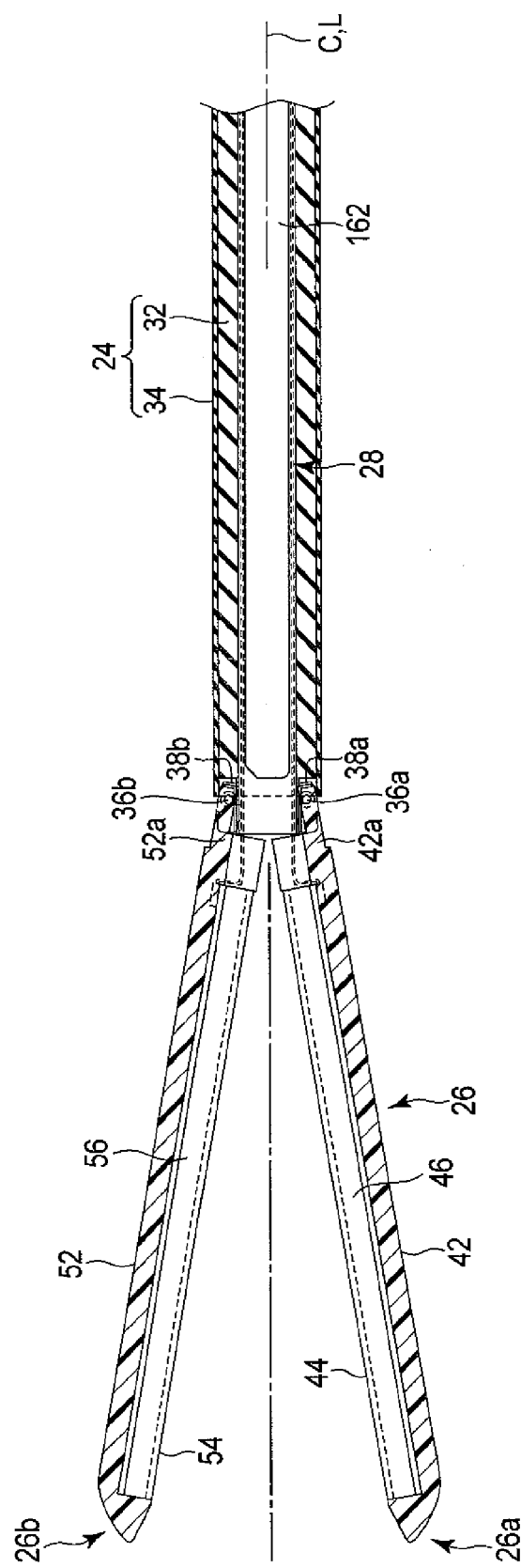
FIG. 9B is a schematic vertical cross-sectional view showing the first and second holding portions in an open state and the ultrasonic probe (second end effector) arranged in the shaft of the treatment device of the medical treatment system according to the modification of the second embodiment.

In this embodiment, an example in which a cutter (hot cutter) 162 and 164 is used as the second end effector 28 has been described; however, as shown in FIGS. 9A to 9C, a probe 172 to which ultrasonic vibration is transferred may be used instead of the cutter 162 and 164. An ultrasonic transducer (not shown) is provided at a proximal end of the probe 172 or that of the drive rod 64, and electric energy from the energy source 14 can be converted into ultrasonic vibration. Thus, a living tissue treated by using heat energy can be further treated, such as coagulated or incised, with the probe 172 by using ultrasonic vibration energy.

Namely, the second end effector 28 according to this embodiment can perform a treatment, such as incision, on a living tissue treated by using heat energy or by using other energy.

Next, the third embodiment will be described with reference to FIGS. 10A to 10C. This embodiment is a modification of the first and second embodiments. Elements which are the same as those described in the first and second embodiments or which have the same functions as those described in the first and second embodiments will be assigned with the same reference symbols, and detailed descriptions thereof will be omitted.

Figure 10A:
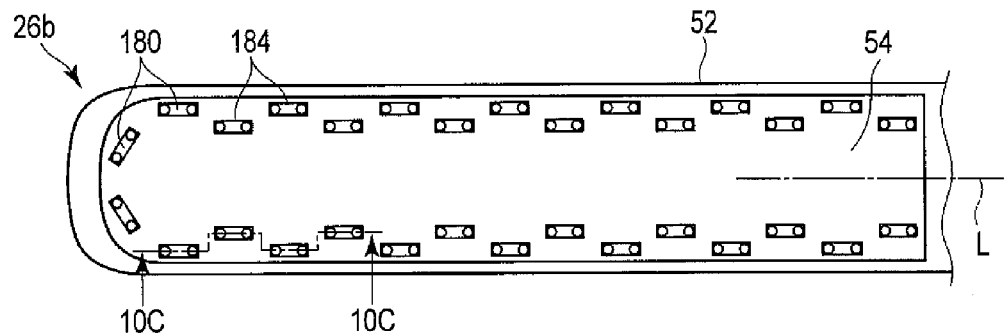
FIG. 10A is a schematic plan view showing a surgical staple (second end effector) arranged in the second holding portion (first end effector) of the treatment device of the medical treatment system according to the third embodiment.
Figure 10B:
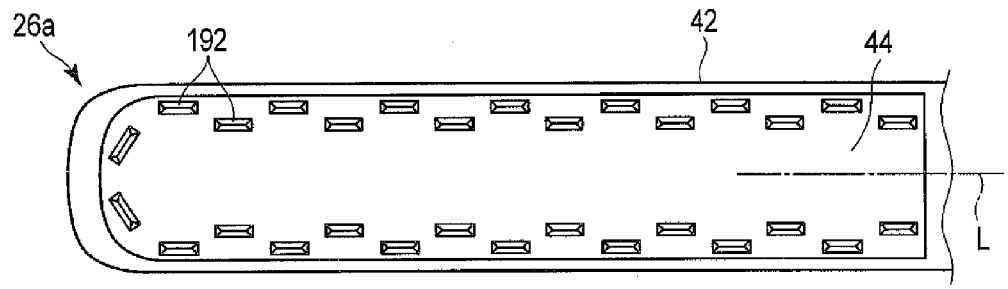
FIG. 10B is a schematic plan view showing the first holding portion (first end effector) of the treatment device of the medical treatment system according to the third embodiment, and a receiving portion which is provided in the first holding portion and receives the surgical staple (second end effector).
Figure 10C:
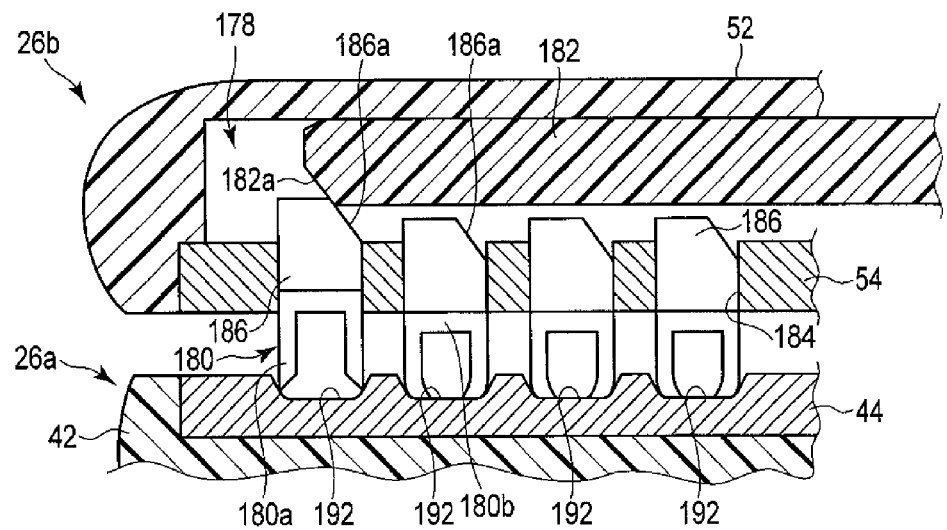
FIG. 10C is a schematic vertical cross-sectional view of the treatment device of the medical treatment system according to the third embodiment taken along line 10C-10C in FIG. 10A.

In this embodiment, as shown in FIGS. 10A to 10C, a surgical staple 180, which is an approximate U-shaped needle, is used as the second end effector 28. The surgical staple 180 is preferably made of, for example, a bioabsorbable material.

As shown in FIGS. 10A to 10C, a plurality of staples 180 are provided in a magazine (second end effector placement portion) 178 between the first jaw 42 and the back surface of energy output portion 44.

As shown in FIG. 10A, a pusher rod 182 having a slope surface 182a is contained in the magazine 178 of the first jaw 42 for discharging the surgical staple (absorbable material) 180 in a manner movable forward and backward. The pusher rod 182 according to this embodiment is provided at the distal end of the drive rod 64 described in the first embodiment.

In the magazine 178, a staple 180 having a pair of legs 180a and an arm 180b which connects the legs 180a is contained in a manner projectable toward the surface of the energy output portion 54 provided on the second jaw 52, with the legs 108a directed to the energy output portion 54. In energy output portion 44, a guide groove (opening) 184 is formed to face the pusher rod 182. In the guide groove 184, a staple pusher 186 having a slope surface 186a inclined similarly to the slope surface 182a of the pusher rod 182 is provided slidably relative to the guide groove 184.

As shown in FIGS. 10B and 10C, a plurality of staple deformation grooves 192 are formed in the holding surface (front surface) 54a of the energy output portion 54 provided on the second jaw 52. Each staple deformation groove 192 has an approximate arc bottom surface so that the pair of legs 180a (see FIG. 10C) of the staple 180 can be each folded and deformed. Therefore, the front surface of the energy output portion 54 provided on the second jaw 2 has a function of an anvil of the staple 180.

The guide grooves 184 shown in FIG. 10A face the staple deformation grooves 192 shown in FIG. 10B, respectively.

In this embodiment, the drive lever 82 described in the first embodiment functions to move the pusher rod 182. In this embodiment, the first and second energy output portions 44 and 54 are preferably a heater or the like.

An advantage of the medical treatment system 10 according to this embodiment will be described. What is described in the first embodiment will be omitted as appropriate.

When the operation portion 76 of the opening-closing lever 72 is brought closer to the other end 22b of the handle main body 20a, the engaging portion 116 of the interlock body 112 is engaged with the engaged portion 102 of the handle main body 20a, as shown in FIG. 5B. At this time, rotation of the opening-closing lever 72 in the second direction β is restricted.

When the opening-closing lever 72 rotates in the first direction α, the outer cylinder 34 moves forward relative to the inner cylinder 32, and the second holding portion 26b closes relative to the first holding portion 26a. Namely, when the opening-closing lever 72 rotates in the first direction α, the first end effector 26 operates. Therefore, the holding surfaces 44a and 54a of the energy output portions 44 and 54 can hold the living tissue. When the pedal 16a of the foot switch 16 is pressed in this state, the living tissue between the energy output portions 44 and 54 is treated by heat energy.

After such treatment, the drive lever 82 is rotated in the first direction γ and brought closer to the opening-closing lever 72, thereby disengaging the engaging portion 116 of the interlock body 112 from the engaged portion 102 of the handle main body 20a. The pair of contact surfaces 88 of the drive lever 82 are brought into contact with the opening-closing lever 72.

When the drive lever 82 rotates in the first direction γ, the pusher rod 182 moves forward. Namely, when the drive lever 82 rotates in the first direction α, the second end effector 28 operates. Therefore, the staple 180 can be fixed to the living tissue being treated using heat energy by folding the pair of legs 180a of the staple 180 to face each other in the staple deformation groove 192 immediately after having the pair of legs 180 pass through the living tissue through the guide groove 184.

When the opening-closing lever 72 is rotated in the second direction β, the drive lever 82 in contact with the opening-closing lever 72 is also rotated in the second direction δ. The engaging portion 116 of the interlock body 112 which moves in accordance with the opening-closing lever 72 is brought farther from the engaged portion 102 of the handle main body 20a.

Therefore, the pusher rod 182 in the magazine 178 can be drawn into the shaft 24 as the first and second holding portions 26a and 26b are opened.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A handle comprising:
a handle main body including a first end and a second end, the first end being closer to a first end effector and a second end effector than the second end;
a first operation input body in front of the second end of the handle main body, the first operation input body being provided on the handle main body, the first operation input body being configured to rotate in a first direction and a second direction to operate the first end effector;
an interlock body rotatable relative to the first operation input body;
an engaging portion provided in the interlock body, the engaging portion being configured to engage the handle main body and to restrict rotation of the first operation input body in the second direction in response to the first operation input body being rotated in the first direction; and
a second operation input body at a position closer to the first end of the handle main body than the first operation input body, the second operation input body being configured to rotate to operate the second end effector, the second operation input body being configured to disengage the engaging portion from the handle main body by pressing the interlock body.

2. The handle of claim 1, wherein the second operation input body comes into contact with the interlock body before coming into contact with the first operation input body in a state where the engaging portion is engaged with the handle main body.

3. The handle of claim 2, wherein the interlock body includes a projection which projects toward the second operation input body in order to contact the second operation input body.

4. The handle of claim 2, wherein the second operation input body includes a projection which projects toward the interlock body in order to contact the interlock body.

5. The handle of claim 1, wherein the second operation input body comes into contact with the first operation input body after coming into contact with the interlock body in a state where the engaging portion is engaged with the handle main body, in response to rotating the second operation input body.

6. The handle of claim 1, wherein the second operation input body includes:
a first contact portion that contacts the first operation input body; and
a second contact portion that travels farther from the first operation input body than the first contact portion and that contacts the interlock body.

7. The handle of claim 1, wherein:
the handle main body has an approximate L-shape; and
the first operation input body is in a lever form configured to be brought closer to and farther from the second end.

8. The handle of claim 1, further comprising:
an elastic member provided between the interlock body and the first operation input body, the elastic member being configured to push the engaging portion to maintain engagement of the engaging portion with the handle main body.

9. The handle of claim 1, wherein the second operation input body disengages the engaging portion from the handle main body by rotating the second operation input body in a direction to approach the first operation input body.

10. A treatment device, comprising:
the handle of claim 1;
a first end effector operated by the first operation input body; and
a second end effector operated by the second operation input body.

11. The treatment device of claim 10, wherein:
the first end effector is configured to perform a function of the first end effector on the living tissue to be treated in response to the first operation input body rotating in the first direction, and configured to stop the function of the first end effector on the living tissue in response to the first operation input body rotating in the second direction; and
the second end effector is configured to perform a function of the second end effector on the living tissue in response to the second operation input body rotating in the fifth direction, and configured to stop the function of the second end effector on the living tissue in response to the second operation input body rotating in a sixth direction.

12. The handle of claim 1, wherein:
the first operation input body is configured to operate at least one of a first holding portion and a second holding portion of the first end effector by an operation; and a living tissue can be held between the first holding portion and the second holding portion.

13. The handle of claim 1, wherein the second operation input body is configured to operate the second end effector by an operation, and a living tissue can be cut by the second end effector.

14. A treatment device comprising:
a handle main body;
a first operation input body provided on the handle main body, the first operation input body being configured to rotate in a first direction and a second direction to operate a first end effector;
an interlock body rotatable relative to the first operation input body;
an engaging portion provided in the interlock body, the engaging portion being configured to engage the handle main body and to restrict rotation of the first operation input body in the second direction in response to the first operation input body being rotated in the first direction; and
a second operation input body configured to rotate to operate a second end effector, the second operation input body being configured to disengage the engaging portion from the handle main body by pressing the interlock body, wherein:
the first end effector includes a first holding portion and a second holding portion that are relatively openable and closable; and
the first operation input body closes the first holding portion and the second holding portion in response to being rotated in the first direction, and opens the first holding portion and the second holding portion in response to being rotated in the second direction.

15. The treatment device of claim 14, wherein:
the second end effector includes a movable body movable toward the living tissue in a state where the first and second holding portions hold the living tissue; and
the second operation input body moves the movable body toward the living tissue held between the first and second holding portions to treat the living tissue when rotated in a fifth direction, and the second operation input body removes the movable body from the living tissue when rotated in a sixth direction.

16. The treatment device of claim 14, wherein:
the handle main body includes a first end and a second end, the first end being closer to the first end effector and the second end effector than the second end;
the first operation input body is provided on the handle main body in front of the second end of the handle main body; and
the second operation input body is provided at a position closer to the first end of the handle main body than the first operation input body.

17. A treatment device comprising:
an end effector having a longitudinal axis, the end effector being configured to perform an appropriate function on a living tissue to be treated;
a handle main body held by an operator, the handle main body including a first end and a second end, the first end being closer to the end effector than the second end;
a first rotational shaft orthogonal to the longitudinal axis;
a first operation input body in front of the second end of the handle main body, the first operation input body being provided rotatably around the first rotational shaft relative to the handle main body, the first operation input body being configured to receive an input of an operation for operating the end effector to perform the appropriate function;
a second rotational shaft orthogonal to the longitudinal axis;
an interlock body rotatable around the second rotational shaft between the first operation input body and the handle main body, the interlock body being configured to move in accordance with the first operation input body in response to an operation input to the first operation input body, and the interlock body being configured to maintain a position of the first operation input body relative to the handle main body;
a third rotational shaft orthogonal to the longitudinal axis; and
a second operation input body at a position closer to the first end of the handle main body than the first operation input body, the second operation input body being provided rotatably around the third rotational shaft, the second operation input body being configured to receive an input of an operation to actuate the end effector to perform the appropriate function and to stop maintaining the position of the first operation input body when brought into contact with the interlock body.

18. The treatment device of claim 17, wherein the second operation input body comes into contact with the interlock body before coming into contact with the first operation input body in a state where the interlock body is engaged with the handle main body, when the second operation input body is rotated around the third rotational shaft.

* * * * *